United States Patent
Maruo et al.

(10) Patent No.: US 10,849,978 B2
(45) Date of Patent: Dec. 1, 2020

(54) PHARMACEUTICAL COMPOSITION FOR ADMINISTRATION TO NASAL MUCOSA

(71) Applicant: Teijin Pharma Limited, Tokyo (JP)

(72) Inventors: Susumu Maruo, Tokyo (JP); Atsuhiro Nagano, Tokyo (JP); Yuko Nonaka, Tokyo (JP); Ryo Furukawa, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 15/750,378

(22) PCT Filed: Oct. 28, 2016

(86) PCT No.: PCT/JP2016/082897
§ 371 (c)(1),
(2) Date: Feb. 5, 2018

(87) PCT Pub. No.: WO2017/073798
PCT Pub. Date: May 4, 2017

(65) Prior Publication Data
US 2018/0228902 A1 Aug. 16, 2018

(30) Foreign Application Priority Data
Oct. 30, 2015 (JP) .................................. 2015-214481

(51) Int. Cl.
*A61K 38/095* (2019.01)
*A61K 47/32* (2006.01)
*A61K 9/08* (2006.01)
*A61K 38/00* (2006.01)
*A61K 9/00* (2006.01)

(52) U.S. Cl.
CPC ............ *A61K 47/32* (2013.01); *A61K 9/0043* (2013.01); *A61K 9/08* (2013.01); *A61K 38/00* (2013.01); *A61K 38/095* (2019.01)

(58) Field of Classification Search
None
See application file for complete search history.

(56) References Cited

U.S. PATENT DOCUMENTS

| | | | | |
|---|---|---|---|---|
| 5,158,761 A | * | 10/1992 | Kamishita | A61K 9/0014 424/209.1 |
| 5,521,283 A | * | 5/1996 | DiMarchi | C07K 14/5759 530/324 |
| 2003/0008019 A1 | | 1/2003 | Nishibe et al. | |
| 2010/0311655 A1 | | 12/2010 | Leonard et al. | |
| 2012/0172304 A1 | * | 7/2012 | Leonard | A61P 5/10 514/11.6 |
| 2013/0045232 A1 | * | 2/2013 | Kido | A61K 9/0043 424/275.1 |
| 2014/0171369 A1 | | 6/2014 | Moberg et al. | |

FOREIGN PATENT DOCUMENTS

| | | | |
|---|---|---|---|
| JP | S60-123426 A | 7/1985 | |
| JP | 2734554 B2 | 3/1998 | |
| JP | 3705620 B2 | 10/2005 | |
| JP | 5142420 B2 | 2/2013 | |
| JP | 2014-515747 A | 7/2014 | |
| JP | 2015-120650 A | 7/2015 | |
| RU | 2 554 814 C2 | 6/2015 | |
| WO | WO-2008150305 A1 * | 12/2008 | ........... A61K 9/0043 |
| WO | 2010/075465 A1 | 7/2010 | |
| WO | 2012140216 A1 | 10/2012 | |

OTHER PUBLICATIONS

Communication, dated Mar. 19, 2019, issued by the Japanese Patent Office in counterpart Japanese application No. 2017-547363.
Prasad et al. "Intranasal Drug Delivery Systems; An Overview", Indian J. Pharm. Sci., 1996, 58(1), pp. 1-8 (8 pages total).
Arora et al., "Permeability issues in nasal drug delivery", DDT vol. 7, No. 18, Sep. 2002, pp. 967-975 (9 pages total).
Ohwaki et al., "Effect of Dose, pH, and Osmolarity on Nasal Absorption of Secretin in Rats. III. In Vitro Membrane Permeation Test and Determination of Apparent Partition Coefficient of Secretin", Chem. Pharm. Bull. 37(12), pp. 3359-3362, 1989 (4 pages total).
Morimoto et al., "Nasal Absorption of Nifedipine from Gel Preparations in Rats", Chem. Pharm. Bull. 35(7), pp. 3041-3044, 1987 (4 pages total).
Kuotsu et al., "Development of Oxytocin Nasal Gel using Natural Mucoadhesive Agent obtained from the Fruits of *Dellinia indica. L*", ScienceAsia vol. 33 (2007), pp. 57-60 (4 pages total).
H. J. Lewis et al., "In-vitro Investigation of the Potential of Mucoadhesive Micro Spheres for the Controlled Nasal Delivery of Oxytocin", Int. J. Pharm. 46, pp. 261-265, 1988 (1 page total).
Jani et al., "Pharmaceutical Approaches Related to Systemic Delivery of Protein and Peptide Drugs: An Overview", International Journal of Pharmaceutical Sciences Reviews and Research, Jan.-Feb. 2012, vol. 12, Issue 1, pp. 42-52 (11 pages total).
Communication, dated Sep. 28, 2018, issued by the European Patent Office in counterpart European Patent Application No. 16860025.2.
Communication, dated Jan. 15, 2020, issued by the Russian Patent Office in Russian Patent Application No. 2018118986 (English Translation).

* cited by examiner

Primary Examiner — Lianko G Garyu
(74) Attorney, Agent, or Firm — Sughrue Mion, PLLC

(57) ABSTRACT

The present invention is intended to provide a nose drop having high absorption of peptide hormone oxytocin or an acid addition salt thereof, or a derivative thereof through nasal mucosa and little safety concern. The present invention is a pharmaceutical composition for administration to nasal mucosa containing oxytocin or an acid addition salt thereof, or a derivative thereof and a carboxyvinyl polymer, characterized by having an osmotic pressure ratio less than 1.

5 Claims, 1 Drawing Sheet
Specification includes a Sequence Listing.

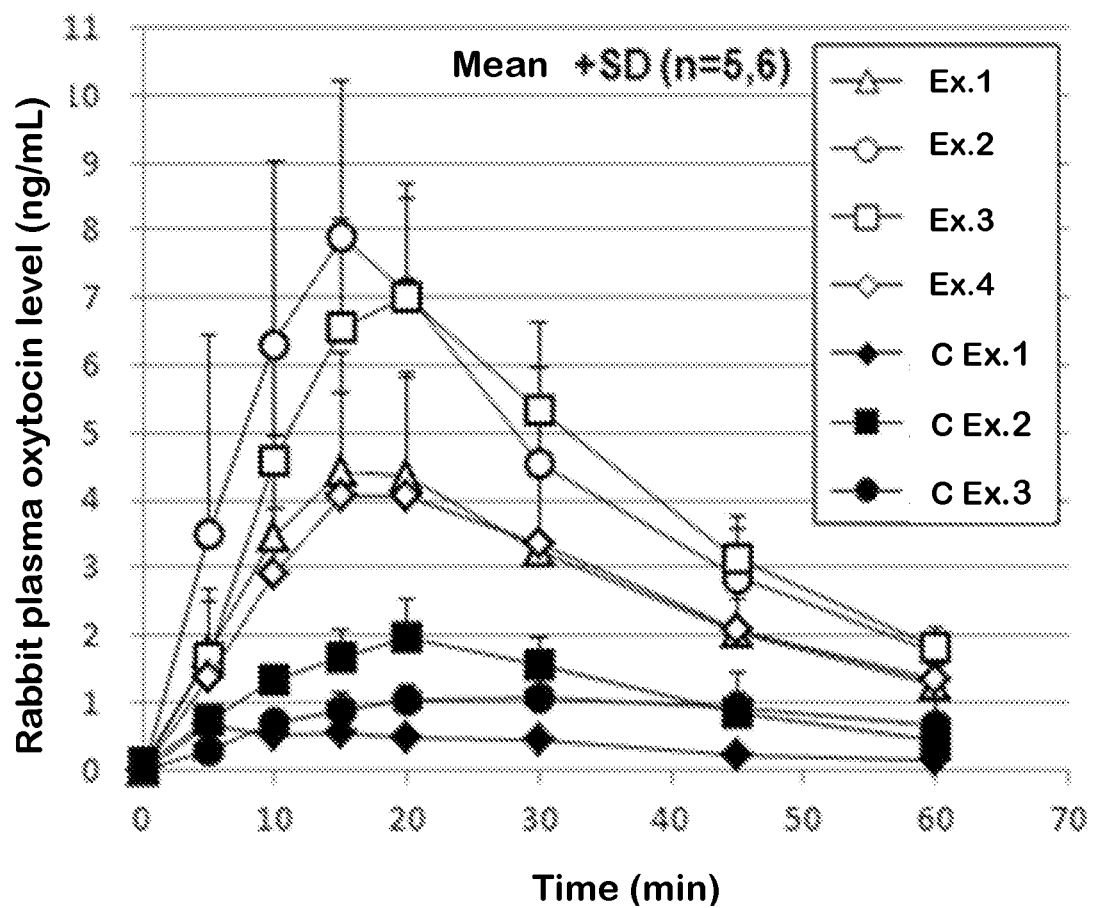

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5
```

PHARMACEUTICAL COMPOSITION FOR ADMINISTRATION TO NASAL MUCOSA

CROSS REFERENCE TO RELATED APPLICATIONS

This application is a National Stage of International Application No. PCT/JP2016/082897 filed Oct. 28, 2016, claiming priority based on Japanese Patent Application No. 2015-214481 filed Oct. 30, 2015, the contents of all of which are incorporated herein by reference in their entirety.

TECHNICAL FIELD

The present invention relates to a pharmaceutical composition for administration to nasal mucosa and particularly relates to a pharmaceutical composition for administration to nasal mucosa containing oxytocin or an acid addition salt thereof, or a derivative thereof as an active ingredient.

BACKGROUND ART

Oxytocin is synthesized in the hypothalamic nucleus of the brain and is a peptide hormone consisting of nine amino acids secreted from pituitary nerve terminals. Oxytocin is a hormone known for a long time, is found to have an action of lactation-promoting effect, and has been used as a nose drop (product name: Syntocinon).

In recent years, since administration of oxytocin as nose drops was reported to have an effect of increasing trust in others, an attempt has been made to develop nose drops as a therapeutic drug that improves social behavior. In the case of a nose drop for promoting lactation, administration is temporary and dosage of oxytocin is low. On the other hand, in the case of a nose drop for improving social behavior, administration may last for a long period and dosage of oxytocin may be higher. Therefore, it is desired to develop a nose drop having a high absorption of oxytocin through nasal mucosa and less safety concern.

So far, as a method for improving transmucosal absorption of oxytocin, PTL 1 proposed a method to use tolmetin or a salt thereof as an absorbefacient. In the examples, although the use of tolmetin sodium as an absorbefacient was shown to improve absorption through the rectal mucous membrane, an absorption-improving effect through nasal mucosa was not shown. In addition, safety concern is not removed for irritation to nasal mucosa and damage to tissue cells in the case of long-term administration of a drug containing an absorbefacient such as tolmetin sodium.

As a method for improving absorption of a peptide or a proteinic drug through nasal mucosa, though not oxytocin itself, a great deal of absorbefacients other than the above-mentioned tolmetin are reported (NPL 1, NPL 2) including bile acids, chelating agents, surfactants, fatty acids, glycosides such as saponin, saccharides such as chitosan, cyclodextrins, phospholipids and the like. In addition, methods using adjustment of physical properties such as osmotic pressure, pH and viscosity of a drug and various polymer substrates are proposed (PTL 2-4).

For example, PTL 2 shows that for a peptide hormone secretin, absorption is improved by preparing a nose drop containing the secretin in which an osmotic pressure ratio is raised to 1-5. Further, for a secretin, it is shown that absorption becomes maximum in an aqueous solution containing 0.46 M sodium chloride (osmotic pressure ratio 3) (NPL 3). Further, PTL 3 shows that for insulin-like growth factor I, absorption is promoted by preparing a liquid formulation for nose drop, containing the insulin-like growth factor I, in which a carboxyvinyl polymer is contained. Conversely, NPL 4 shows that, although absorption of nifedipine occurs immediately by using polyethylene glycol as a substrate, absorption is low when a carboxyvinyl polymer is used. Note that a carboxyvinyl polymer is not contained in the above-mentioned Syntocinon: a commercial product of a transnasal agent of oxytocin. Further, PTL 4 shows that for a peptide hormone salmon calcitonin, absorption is improved by preparing a nose drop, containing a peptide hormone salmon calcitonin, in which crystalline cellulose as a water-insoluble and/or a low-water-soluble material is contained, and osmotic pressure (osmolality) is 60 mOsm or less. On the other hand, the osmolality of the above-mentioned Syntocinon, a commercial product of a transnasal agent of oxytocin, is high at 629 mOsm (osmotic pressure ratio 2).

Though methods using osmotic pressure and polymer substrates are expected to reduce irritation to nasal mucosa and damage to tissue cells for the case of long-term administration and are favorable from the viewpoint of safety, it was not clear whether these methods proposed so far can improve absorption of oxytocin through nasal mucosa, because a peptide in general has low permeability through nasal mucosa due to its high molecular weight, and, as mentioned above, effects by osmotic pressure and a polymer substrate vary depending on the kind of peptide.

CITATION LIST

Patent Literature

[PTL 1]
Japanese Patent Publication No. 3705620
[PTL 2]
Japanese Unexamined Patent Application Publication No. Sho 60-123426
[PTL 3]
Japanese Patent Publication No. 2734554
[PTL 4]
Japanese Patent Publication No. 5142420

Non Patent Literature

[NPL 1]
Indian Journal of Pharmaceutical Sciences. 1996, 58(1), pp 1-8
[NPL 2]
DDT Vol. 7, No. 18 Sep. 2002, pp 967-975
[NPL 3]
Chem. Pharm. Bull. 37 (12) 3359-3362 (1989)
[NPL 4]
Chem. Pharm. Bull. 35, 304-1 (1987)

SUMMARY OF INVENTION

Technical Problem

An object of the present invention is to develop a nose drop that exhibits high absorption of oxytocin or an acid addition salt thereof, or a derivative thereof through nasal mucosa and has little safety concern.

Solution to Problem

As a result of earnest studies to solve the above-mentioned problem, the present inventors have found that the above-mentioned object of the present invention is achieved by preparing a pharmaceutical composition for administration to nasal mucosa that is an aqueous formulation containing oxytocin or an acid addition salt thereof, or a derivative thereof and further contains a carboxyvinyl polymer and is characterized by having an osmotic pressure ratio less than 1, thereby completing the present invention.

In other words, the present invention is a pharmaceutical composition for administration to nasal mucosa containing oxytocin or an acid addition salt thereof, or a derivative thereof and a carboxyvinyl polymer, and characterized by having an osmotic pressure ratio less than 1.

In addition, the present invention further contains a salt, and preferably has the viscosity of 100-10000 mPa·s, and more preferably 1500-2800 mPa·s.

Further, the present invention preferably has an osmolality of 0-200 mOsm.

Further, the present invention preferably contains 0.1-2.0 wt % of a carboxyvinyl polymer based on the amount of a pharmaceutical composition for administration to nasal mucosa.

Further, the present invention preferably contains 0.01-20 mM of a salt based on the amount of a pharmaceutical composition for administration to nasal mucosa.

Advantageous Effects of Invention

According to the present invention, it is possible to obtain a nose drop that exhibits high absorption of oxytocin through nasal mucosa and has little safety concern.

BRIEF DESCRIPTION OF DRAWINGS

FIG. 1 The graph shows a temporal change of the oxytocin concentration in rabbit plasma for each Example and Comparative Example.

DESCRIPTION OF EMBODIMENTS

In a pharmaceutical composition of the present invention, a remarkable absorption improvement of oxytocin or an acid addition salt thereof, or a derivative thereof cannot be obtained by only lowering osmolality of an aqueous composition containing oxytocin or an acid addition salt thereof, or a derivative thereof without adding a carboxyvinyl polymer. Nor can a remarkable absorption improvement of oxytocin or an acid addition salt thereof, or a derivative thereof be obtained by leaving the osmotic pressure ratio of an aqueous composition to 1 (isotonic) or more and only adding a carboxyvinyl polymer. That is, in an aqueous composition containing oxytocin or an acid addition salt thereof, or a derivative thereof, a remarkable absorption improvement is achieved by adding a carboxyvinyl polymer and, at the same time, lowering the osmotic pressure ratio to less than 1.

In the present invention, oxytocin, the active ingredient, is a peptide having an amino acid sequence of Cys-Tyr-Ile-Gln-Asn-Cys-Pro-Leu-Gly (SEQ ID NO: 1). Oxytocin may be an acid addition salt thereof, and a typical example of an acid addition salt include acetate, though not limited thereto. Oxytocin derivatives include demoxytocin and carbetocin, an acid addition salt thereof, a derivative in which polysaccharide and polyethylene glycol are added thereto as a linker, and the like, though not limited thereto. Besides, the content of oxytocin or an acid addition salt thereof, or a derivative thereof in the present invention can be determined depending on a target disease of treatment and a therapeutic purpose such as symptom, an age and the like of a target patient, and, though not determined unconditionally, for example, can be determined to 0.001-1.0 wt % based on the amount of the drug, and preferably 0.004-0.4 wt %.

The osmotic pressure ratio of the composition of the present invention is less than 1. In the present invention, the osmotic pressure ratio is defined as the ratio of the osmolality of the composition of the present invention to 286 mOsm, the osmolality of a physiological saline (0.900 g of sodium chloride/100 mL of water), and is used as an index of isotonicity. The osmolality of a physiological saline is almost the same as the normal osmolality of the mucosal tissue at the dosage point of a living body. The osmolality of the mucosal tissue of a living body varies, and thus isotonicity (In the present invention, isotonicity means having the same osmolality as a mucosal tissue of a living body.) is defined as 286 mOsm±5%, that is 272-300 mOsm: particularly an osmotic pressure ratio within this range is regarded as 1. The osmolality of the composition of the present invention is preferably 0-200 mOsm, more preferably 0-150 mOsm, further becomes more preferable in the order of 0-100 mOsm, 0-70 mOsm, 0-50 mOsm, 0-30 mOsm, and 0-10 mOsm. Note that the osmolality in the present invention is determined as osmolality (mol/kg) using a cryoscopic method, which can be regarded as numerically equal to osmolarity (mol/L) in the dilute concentration region up to at least about 1000 mOsm. Thus, the value is the same even if the unit is expressed in osmolarity (mol/L). Further, in the present invention, osmolality may be described as osmotic pressure.

An osmolyte can be used to adjust osmotic pressure in the present invention. Examples of osmolyte, not limited in particular as long as being water-soluble, include saccharide such as glucose, fructose and maltose, alcohols such as glycerine, sugar alcohols such as D-sorbitol, D-mannitol and xylitol, salts such as sodium chloride, and the like. These can be used singly or as a mixture of one kind or two or more kinds.

In the present invention, a carboxyvinyl polymer is not limited as far as it is a hydrophilic polymer having acrylic acid as a main unit structure, water-soluble or swellable and capable of thickening. It may be partially bridged and a copolymer containing other unit structure. The carboxyvinyl polymer preferably has a carboxyl group content of 50-75%. Also, viscosity of a 0.5 wt % aqueous solution of the polymer is preferably 20,000-50,000 (25° C., pH 7.3-7.8). Specifically, included are Carbopol® 910, 934, 934P, 940, 941, 971PNF, 974PNF and the like of the Lubrizol Corporation. Among them, Carbopol® 934, 934P, 974PNF have a high thickening effect, and are more preferable. Carboxyvinyl polymers of other companies having the same property are also similarly preferable.

Also, the content of the carboxyvinyl polymer in the present invention can be optionally set within the range that enables the drug to be sprayed by a nasal administration device, and is preferably 0.1-2.0 wt % based on the amount of the drug, more preferably 0.2-1.0 wt %, and further becomes more preferable in the order of 0.3-1.0 wt % and 0.3-0.6 wt %.

Further, an aqueous composition containing oxytocin or an acid addition salt thereof, or a derivative thereof, further containing a carboxyvinyl polymer and having an osmotic pressure ratio less than 1, preferably has a viscosity of 100-10000 mPa·s to enhance absorption of an active ingredient through nasal mucosa. When the viscosity is less than 100 mPa·s, it becomes hard to obtain a sufficient improving effect for absorption of oxytocin through nasal mucosa, and when the viscosity exceeds 10000 mPa·s, it becomes hard to spray manually due to increased push pressure during administration with a nasal administration device, and it becomes hard to spray uniformly due to an increased droplet particle diameter during spraying, which is not preferable.

The viscosity in the present invention is adjusted, within the range that enables the drug to be sprayed by a nasal administration device, by a salt preferably to 100-10000 mPa·s, and is further preferably 200-10000 mPa·s, more preferably 100-5000 mPa·s, further more preferably 500-5000 mPa·s, and further becomes more preferable in the order of 1000-3000 mPa·s, 1500-2800 mPa·s and 1800-2500 mPa·s. The salts in the present invention for adjusting viscosity, though not limited in particular as long as being water-soluble, include, for example, inorganic salts such as sodium chloride, potassium chloride, calcium chloride, magnesium chloride, zinc chloride, potassium carbonate, magnesium sulfate and sodium hydrogenphosphate, and organic salts such as sodium citrate, sodium edetate, potassium sorbate, arginine hydrochloride, lysin hydrochloride, sodium aspartate, magnesium aspartate, sodium caprylate, sodium gluconate, sodium gluconate, sodium glutamate, sodium succinate, sodium acetate, calcium acetate, sodium tartrate and sodium malate. The salts may be added in one kind or more kinds. Viscosity that is imparted by the addition of the above-mentioned carboxyvinyl polymer is reduced by the addition of the salts, and adjusted to an intended particular viscosity by selecting the kind and amount of the salts to be added. Adjustment of viscosity is not necessarily performed by salt addition but may be performed by agitation and the like.

Also, the salt content in the present invention can be optionally set within the range such that the viscosity of an aqueous solution containing a carboxyvinyl polymer is adjusted to a preferable range such as 100-10000 mPa·s. In addition, during the addition of a carboxyvinyl polymer, the salt as is may be added in advance or at the same time, or may be added after the addition of a carboxyvinyl polymer. Also, a salt of an acidic substance and a basic substance may be added separately. The amount of the salt to be added to the composition is preferably 0.01-20 mM and more preferably 0.1-4 mM.

The pH in the present invention is preferably pH 2.5-7.5, more preferably pH 3.0-6.0, and particularly preferably pH 3.5-5.0. Also, the pH regulators, though not limited in particular as long as being water-soluble and capable of adjusting pH within the above-mentioned range, include specifically, for example, sodium hydroxide, arginine, hydrochloric acid, citric acid, boric acid, tartaric acid, carbonic acid, phosphoric acid, a salt thereof, and the like. These can be used singly or as a mixture of one kind or two or more kinds.

Also, existing well-known preservatives may be added to the pharmaceutical composition for administration to nasal mucosa in the present invention as needed. Examples of the preservatives include methyl parahydroxybenzoate, ethyl parahydroxybenzoate, propyl parahydroxybenzoate, butyl parahydroxybenzoate, benzalkonium chloride, potassium sorbate, sodium edetate, chlorobutanol, phenoxyethanol, sodium benzoate, and the like, and preferably parabens such as methyl parahydroxybenzoate, propyl parahydroxybenzoate and the like. These can be used singly or as a mixture of one kind or two or more kinds.

Furthermore, existing well-known stabilizer, anti-oxidant, odor improving agent, and the like may be added to the composition in the present invention as needed. The additives include specifically, for example, stabilizers such as citric acid, sodium citrate, sodium edetate, sodium erythorbate, anti-oxidants such as ascorbic acid and tocopherol, and odor improving agent such as menthol. These can be used singly or as a mixture of one kind or two or more kinds.

Since the nose drop in the present invention contains oxytocin or an acid addition salt thereof, or a derivative thereof as an active ingredient, administration of a nose drop in the present invention is effective for prevention or treatment of the diseases, for example, such as autistic spectrum disorder, schizophrenia, fragile X syndrome, reactive attachment disorder, obesity, and the like.

The composition of the present invention is manufactured, for example, by dissolving oxytocin or an acid addition salt thereof, or a derivative thereof in water and adding thereto an aqueous solution of a carboxyvinyl polymer separately prepared by dissolving a carboxyvinyl polymer in water, and further adjusting the pH of the solution to an intended value by adding an aqueous solution of sodium hydroxide.

EXAMPLES

The present invention is explained below in Examples, but the present invention is not limited thereto. Note that, in Examples, part means part by weight and % means wt %.

Example 1

To a glass vessel, 0.054 g of oxytocin acetate (0.048 g of oxytocin) was added and 30 g of purified water was added to dissolve the mixture. Then, 40 g of 1% aqueous carboxyvinyl polymer solution was added to the acetate solution. To the solution, 2.40 mL of 0.1 M sodium hydroxide solution was added to adjust pH to 4.0 while measuring the pH value using a pH meter, and purified water was added to make a total amount of 100 g, and thus an aqueous pharmaceutical composition for administration to nasal mucosa was prepared. As for the composition, osmolality was measured using an osmolar analyzer (ARKRAY, Inc., OM-6060), and viscosity was measured at 25° C. using an E-type viscometer (TOKI SANGYO CO., LTD., TVE-25). The composition list, pH, osmolality, and viscosity of the prepared pharmaceutical composition are shown in Table 1. Further, 100 μL of the prepared aqueous pharmaceutical composition for administration to nasal mucosa was sprayed on a unilateral nasal cavity of a rabbit (Japanese white rabbit, male, about 3 kg in weight) using a commercial administration device for a liquid nose drop drug. About 1 mL of blood was sampled from an ear vein before administration and at 5 min, 10 min, 15 min, 20 min, 30 min, 45 min and 60 min after administration, and the plasma oxytocin level was determined by an LC-MS/MS method. The plasma oxytocin level profile until 60 minutes after spraying is shown in FIG. 1, and the mean and the standard deviation of AUC0-60 min. (among 5 or 6 rabbits) obtained from a time-concentration curve are shown in Table 1. Note that AUC0-60 min. in the present application is an area under time-concentration curve in the range of 0-60 min.

Example 2

To a glass vessel, 85 g of purified water was added, 0.054 g of oxytocin acetate (0.048 g of oxytocin) and 0.50 g of carboxyvinyl polymer were added and dissolved while stirring with a stirrer. To the solution, 3.00 mL of 0.1 M sodium hydroxide solution was added to adjust pH to 4.0 while measuring the pH value using a pH meter, 0.60 mL of physiological saline was added to adjust the viscosity, and purified water was added to make a total amount of 100 g, and thus an aqueous pharmaceutical composition for administration to nasal mucosa was prepared. Osmolality and viscosity were measured in a similar manner to Example 1. The composition list, pH, osmolality, and viscosity of the prepared pharmaceutical composition are shown in Table 1. The prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

Example 3

To a glass vessel, 95.55 g of purified water was added, 0.054 g of oxytocin acetate (0.048 g of oxytocin) and 0.50 g of carboxyvinyl polymer were added and dissolved while stirring with a stirrer. To the solution, 0.60 mL of saline was added to adjust the viscosity, 3.30 mL of 0.1 M sodium hydroxide solution was added to adjust a pH to 4.0 while measuring the pH value using pH meter, and thus an aqueous pharmaceutical composition for administration to nasal mucosa was prepared. Osmolality and viscosity were measured in a similar manner to Example 1. The composition list, pH, osmolality, and viscosity of the prepared pharmaceutical composition are shown in Table 1. The prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

Example 4

An aqueous pharmaceutical composition for administration to nasal mucosa was prepared in a similar manner to Example 2, except that the amount of saline for adjusting pH was 2.30 mL and the amount of 0.1 M sodium hydroxide solution for adjusting viscosity was 3.30 mL. Osmolality was measured in a similar manner to Example 1. Viscosity was measured at 25° C. using a B-type viscometer (Brookfield company, LVDV-II+). The composition list, pH, osmolality, and viscosity of the prepared pharmaceutical composition are shown in Table 1. Also, the prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

Comparative Example 1

A pharmaceutical composition was prepared by adding oxytocin acetate to Syntocinon (product name) to adjust the oxytocin level to 0.048%. pH and osmolality of the prepared aqueous pharmaceutical composition for administration to nasal mucosa were measured in a similar manner to Example 1. The pH and osmolality of the pharmaceutical composition prepared are shown in Table 1. Also, the prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

Comparative Example 2

To a glass vessel, 140 g of purified water was added, 20 g of 0.1% aqueous benzalkonium chloride solution, 20 g of purified water, and 0.108 g of oxytocin acetate were added and dissolved while stirring with a stirrer. To the solution, 1.0 mL of 0.1 M hydrochloric acid was added to adjust pH to 4.0 while measuring the pH value using a pH meter, purified water was added to make a total amount of 200 g, and thus an aqueous pharmaceutical composition for administration to nasal mucosa was prepared. Osmotic pressure and viscosity were measured in a similar manner to Example 4. The composition list, pH, osmolality, and viscosity of the prepared pharmaceutical composition are shown in Table 1. Also, the prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

Comparative Example 3

To a glass vessel, 90 g of purified water was added, 0.26 g of carboxyvinyl polymer was added and dissolved while stirring with a stirrer, and 4.80 g of sorbitol and 0.054 g of oxytocin acetate were added and dissolved. To the solution, 0.70 mL of 0.1 M sodium hydroxide solution was added to adjust pH to 4.0 while measuring the pH value using a pH meter, purified water was added to make a total amount of 100 g, and thus an aqueous pharmaceutical composition for administration to nasal mucosa was prepared. Osmolality and viscosity were measured in a similar manner to Example 4. The composition list, pH, osmolality, and viscosity of the prepared pharmaceutical composition are shown in Table 1. Also, the prepared aqueous pharmaceutical composition for administration to nasal mucosa was sprayed on a unilateral nasal cavity of a rabbit and blood was sampled over time in a similar manner to Example 1. The plasma oxytocin level profile obtained from the measurement of the plasma oxytocin level is shown in FIG. 1, and AUC0-60 min. is shown in Table 1.

TABLE 1

| | | Example 1 | Example 2 | Example 3 | Example 4 |
|---|---|---|---|---|---|
| Composition (%) | Oxytocin | 0.048 | 0.048 | 0.048 | 0.048 |
| | Carboxyvinyl polymer | 0.40 | 0.50 | 0.50 | 0.50 |
| | Benzalkonium chloride | — | — | — | — |
| | Sorbitol | — | — | — | — |

TABLE 1-continued

|  |  | | | | |
|---|---|---|---|---|---|
| | 0.1M sodium hydroxide solution | 2.40 | 3.00 | 3.30 | 3.30 |
| | 0.1M hydrochloric acid | — | — | — | — |
| | Saline | — | 0.60 | 0.60 | 2.30 |
| | Purified water | 97.15 | 95.85 | 95.55 | 93.85 |
| Osmolality (mOsm) | | 2 | 3 | 3 | 9 |
| Viscosity (mPa·s) | | 2953 | 1917 | 2492 | 106 |
| pH | | 4.1 | 4.0 | 4.0 | 3.9 |
| AUC(0-60 min) ± standard deviation (ng·min/mL) | | 159.5 ± 54.3 | 253.5 ± 74.1 | 243.9 ± 50.1 | 155.2 ± 48.5 |

| | | Comparative Example 1 | Comparative Example 2 | Comparative Example 3 |
|---|---|---|---|---|
| Composition (%) | Oxytocin | 0.048 | 0.048 | 0.048 |
| | Carboxyvinyl polymer | — | — | 0.26 |
| | Benzalkonium chloride | —[1] | 0.01 | — |
| | Sorbitol | | — | 4.80 |
| | 0.1M sodium hydroxide solution | | — | 0.7 |
| | 0.1M hydrochloric acid | | 0.5 | — |
| | Saline | | — | — |
| | Purified water | | 99.44 | 94.19 |
| Osmolality (mOsm) | | 629 | 0 | 276 |
| Viscosity (mPa·s) | | —[2] | 2 | 53 |
| pH | | 4.0 | 4.0 | 4.0 |
| AUC(0-60 min) ± standard deviation (ng·min/mL) | | 22.6 ± 5.4 | 69.0 ± 14.0 | 49.5 ± 20.4 |

[1] Prepared by adding oxytocin acetate to Syntocinon (product name) to adjust the oxytocin level to 0.048%
[2] Not measured As shown in Example 1, the composition prepared by using a carboxyvinyl polymer in which the osmotic pressure ratio was adjusted to less than 1 had a remarkably high transnasal absorption that is 7 times as high as the composition (Comparative Example 1), which was prepared by using Syntocinon (product name), the only commercial product of an oxytocin transnasal agent, and only by adjusting the oxytocin level to the same level as in the Example. In addition, as shown in Examples 2-4, the compositions prepared to contain a carboxyvinyl polymer and have an osmotic pressure ratio less than 1, in which the values of the viscosity were adjusted to 1917, 2492, 106 mPa·s by adding salts, had remarkably high transnasal absorption. The AUC (0-60 min.) values were particularly high in Examples 2 and 3, wherein it was shown that the composition prepared to exhibit a viscosity of 1500-2800 mPa·s by adding a salt had a particularly high improving effect on the transnasal absorption. On the other hand, as shown in Comparative Example 1, the composition prepared by adding oxytocin to Syntocinon (product name) to make the oxytocin concentration same as in the Example, had a low nasal absorption. In addition, as shown in Comparative Example 2, high transnasal absorption was not exhibited in the composition prepared without using a carboxyvinyl polymer and only adjusted to have the osmotic pressure ratio of less than 1. In addition, as shown in Comparative Example 3, high transnasal absorption was not exhibited in the composition prepared by using a carboxyvinyl polymer and adjusted to have the osmotic pressure ratio close to isotonicity.

Example 5

To a glass vessel, 83.55 g of a solution consisting of 0.036% methyl parahydroxybenzoate/0.018% propyl parahydroxybenzoate was added, 0.282 g of oxytocin acetate (0.248 g of oxytocin) and 0.60 g of carboxyvinyl polymer were added thereto and dissolved while stirring with a stirrer. To the solution, 3.2 mL of 0.1 M sodium hydroxide solution was added to adjust pH to 4.0 while measuring the pH value using a pH meter, and purified water was added to make a total amount of 100 g, and thus an aqueous pharmaceutical composition for administration to nasal mucosa was prepared. Osmolality and viscosity were measured in a similar manner to Example 1. The composition list, pH, osmolality, and viscosity of the prepared pharmaceutical composition are shown in Table 2. Further, 100 µL of the prepared aqueous pharmaceutical composition for administration to nasal mucosa was sprayed on a unilateral nasal cavity of a rabbit (Japanese white rabbit, male, about 3 kg in weight, 20 rabbits) using a commercial administration device for a liquid nose drop drug. Approximately 0.5 mL of cerebrospinal fluid (CSF) was sampled from cisterna magna at 0.5, 1, 2, 4 and 8 hours after administration, and the oxytocin level in CSF was determined by an LC-MS/MS method.

Example 6

To a glass vessel, 83.87 g of a solution consisting of 0.036% methyl parahydroxybenzoate/0.018% propyl parahydroxybenzoate was added, 0.283 g of oxytocin acetate (0.249 g of oxytocin) and 0.60 g of carboxyvinyl polymer were added thereto and dissolved while stirring with a stirrer. To the solution, 0.8 mL of physiological saline was added to adjust the viscosity, 3.9 mL of 0.1 M sodium hydroxide solution was added to adjust pH to 4.0 while measuring the pH value using a pH meter, and purified water was added to make a total amount of 100 g, and thus an aqueous pharmaceutical composition for administration to nasal mucosa was prepared. Osmolality and viscosity were measured in a similar manner to Example 1. The composition list, pH, osmolality, and viscosity of the prepared pharmaceutical composition are shown in Table 2. The prepared aqueous pharmaceutical composition for administration to nasal mucosa, in a similar manner to Example 5, was sprayed on a unilateral nasal cavity of a rabbit (Japanese white rabbit, male, about 3 kg in weight, 20 rabbits), CSF was sampled from cisterna magna over time, and the oxytocin level in CSF was determined by an LC-MS/MS method.

TABLE 2

|  |  | Example 5 | Example 6 |
|---|---|---|---|
| Composition (%) | Oxytocin | 0.248 | 0.249 |
|  | Carboxyvinyl polymer | 0.60 | 0.60 |
|  | 0.036% methyl parahydroxybenzoate/0.018% propyl parahydroxybenzoate solution | 83.54 | 83.86 |
|  | 0.1M sodium hydroxide solution | 3.2 | 3.9 |
|  | Saline | — | 0.8 |
|  | Purified water | 12.37 | 10.55 |
| Osmolality (mOsm) |  | 16 | 16 |
| Viscosity (mPa · s) |  | 4141 | 2116 |
| pH |  | 4.1 | 4.1 |

As is shown in Example 5, for the composition prepared to contain a carboxyvinyl polymer and have an osmotic pressure ratio less than 1, the half-life of the oxytocin level in cerebrospinal fluid (CSF) after transnasal administration was 1.8 h and twice or more as that of the blood level. In addition, as shown in Example 6, for the compositions prepared to contain a carboxyvinyl polymer, have an osmotic pressure ratio less than 1, and exhibit a viscosity adjusted by adding salts, the half-life of the oxytocin level in cerebrospinal fluid (CSF) after transnasal administration was 2.3 h and twice or more as that of the blood level. That is, long-lastingness of the oxytocin level in CSF was shown: the oxytocin level in CSF is maintained at high level for an extended period. Incidentally, for the drug of Comparative Example 1, the oxytocin level in CSF was below measurement sensitivity in most individuals.

This indicates that, in an aqueous composition containing oxytocin or an acid addition salt thereof, or a derivative thereof, a remarkable migration property of oxytocin to cerebrospinal fluid and long-lastingness of the oxytocin level in cerebrospinal fluid are achieved by adding a carboxyvinyl polymer and, at the same time, lowering the osmotic pressure ratio to less than 1. According to the present invention, a nose drop can be obtained that maintains the oxytocin level in cerebrospinal fluid high for an extended period.

INDUSTRIAL APPLICABILITY

A pharmaceutical composition for administration to nasal mucosa of the present invention contains oxytocin or an acid addition salt thereof, or a derivative thereof as an active ingredient and can be used as a nose drop having high absorption of oxytocin through nasal mucosa and little safety concern.

---

---

The invention claimed is:

1. A pharmaceutical composition for administration to nasal mucosa, comprising:
   oxytocin or an acid addition salt thereof, or a derivative thereof, and a carboxyvinyl polymer,
   wherein an osmolality of the composition is 0-100 mOsm.

2. The pharmaceutical composition for administration to nasal mucosa according to claim 1, further comprising a salt, wherein a viscosity of the composition is 100-10000 mPa·s.

3. The pharmaceutical composition for administration to nasal mucosa according to claim 2, wherein the viscosity is 1500-2800 m·Pas.

4. The pharmaceutical composition for administration to nasal mucosa according to claim 1, wherein 0.1-2.0 wt % of the carboxyvinyl polymer based on the amount of the pharmaceutical composition for administration to nasal mucosa is contained.

5. The pharmaceutical composition for administration to nasal mucosa according to claim 1, wherein 0.01-20 mM of the salt is contained in the pharmaceutical composition for administration to nasal mucosa.

* * * * *